United States Patent [19]
Bantel

[11] Patent Number: 5,111,046
[45] Date of Patent: May 5, 1992

[54] APPARATUS AND METHOD FOR INSPECTING COOLING HOLES

[75] Inventor: Thomas E. Bantel, Cincinnati, Ohio

[73] Assignee: General Electric Company, Cincinnati, Ohio

[21] Appl. No.: 670,658

[22] Filed: Mar. 18, 1991

[51] Int. Cl.$^5$ .............................................. G01N 25/72
[52] U.S. Cl. ................................... 250/330; 250/340; 374/5
[58] Field of Search ............... 250/340, 341, 330, 334; 374/5

[56] References Cited

U.S. PATENT DOCUMENTS 3,566,669  3/1971  Lawrence et al. ..................... 374/5
4,644,162  2/1987  Bantel et al. ........................ 250/340

FOREIGN PATENT DOCUMENTS 2125556  3/1984  United Kingdom .

OTHER PUBLICATIONS

"Infrared Scanner Detects Coating Defects", Materials Engineering, Oct. 1983.
"Thermal Diffusivity Measures Thin Films", Lasers & Applications, May 1984, p. 36.
"British Seek Way to Test Composites", Tech Update, Jul. 1983.

Primary Examiner—Carolyn E. Fields
Attorney, Agent, or Firm—Charles L. Moore, Jr.; Jerome C. Squillaro

[57] ABSTRACT

A method and apparatus for inspecting a channel through a workpiece or cooling holes through the surface of a gas turbine engine are disclosed. The gas turbine engine blade is mounted in a fixture such that a heated gas may be forced into the hollow interior of the blade during a heat-up cycle, and after a predetermined period of time, a solenoid valve switches to shut off the heated gas and to permit a chilled gas to be forced into the hollow interior of the blade for a cool-down cycle. An imaging infrared radiometer generates a series of images of the blade during both the heat-up and cool-down cycles. A selected group of parameters are determined from the series of images generated by the IR radiometer and defects within the cooling holes may then be detected by analyzing the parameters, such as a transient response of the infrared signature of the cooling holes during both the heat-up and the cool-down cycles.

19 Claims, 3 Drawing Sheets

APPARATUS AND METHOD FOR INSPECTING COOLING HOLES

BACKGROUND OF THE INVENTION

The present invention relates to the detection of blocked or defective cooling holes in a gas turbine engine blade and, more particularly, to an apparatus and method for inspecting the cooling holes of a gas turbine engine blade by using infrared thermography.

Referring to FIG. 1, a gas turbine engine blade 10 has a multiplicity of cooling channels or holes 12 formed therein to permit cooling of the blade during engine operation. The cooling holes 12 extend from an exterior surface 14 of blade 10 into a hollow interior 16 or plenum of the blade 10. The blade hollow interior includes a plurality of interior walls 18 or baffles to direct cooling air, indicated by arrows 20, through the interior of blade 10 and out cooling holes 12 to create cooling air streams, indicated by arrows 22. Cooling air 20 absorbs heat within the interior 16 of blade 10 and also from the walls surrounding cooling holes 12 and cooling air streams 22 exiting holes 12 flow over the exterior surface 14 to further cool the blade.

In order to function properly, the cooling holes 12 must be constructed to a known configuration because the distribution of airflow must be controlled to achieve proper cooling of the blade during engine operation. Thus, the cooling holes must not be blocked or even partially blocked to provide sufficient and uniform cooling air distribution through blade interior 16 and across the exterior 14 of blade 10. Inspection of cooling holes 12 to detect blockages is difficult because of the small size of the holes; a typical hole diameter is about 12 mils (0.3 mm.). A wire or pin diameter gage may be used to inspect the cooling holes for blockage but this method is time consuming, tedious and labor intensive. Additionally, the wire or pin gauges can break and pieces of the gauge can become trapped within the interior plenum or the cooling hole and therefore block the hole.

A method and apparatus for inspecting cooling holes using infrared thermography is disclosed and claimed in U.S. Pat. No. 4,644,162, issued Feb. 17, 1987, assigned to the same assignee as the present invention, and incorporated herein in its entirety by reference. This patent discloses forcing a heated gas through a relatively cooler cooling hole, measuring the infrared signature of the cooling holes during the transient with a scanning infrared radiometer, and comparing the measured radiation intensity with a reference. The patent also contemplates forcing a cool gas through a relatively warmer channel and measuring the radiation intensity emitted by the cooling holes but the patent does not disclose the advantages derived by measuring the radiation intensity of the cooling holes during a heat-up cycle, when a heated gas is forced through the cooling holes and also during a cool-down cycle, when a chilled gas is forced through the cooling holes immediately after the heat-up cycle.

Observing only a heated gas forced through the cooling holes or only a cool gas forced through relatively warmer cooling holes can give rise to erroneous characterization of a blocked hole or channel. Additionally, inferences as to the specific nature of the cooling hole defect may be difficult to make by measuring the infrared signature during the transient of only either a heat-up cycle or a cool-down cycle independent of one another.

SUMMARY OF THE INVENTION

It is, accordingly, a primary object of the present invention to provide a novel method and apparatus for inspecting channels or openings through a workpiece which are not subject to the foregoing disadvantages.

It is another object of the present invention to provide a novel method and apparatus for detecting blocked or partially blocked or defective cooling holes in a gas turbine engine blade.

It is a further object of the present invention to provide a method and apparatus for inspecting the cooling holes of a gas turbine engine blade which provides some information as to the nature of the defect in the cooling hole.

In accordance with the present invention, a method of inspecting a channel, includes the steps of: forcing a heated gas of a selected temperature through the channel for a predetermined time period to cause a heat-up cycle; measuring selected parameters from an infrared signature of the channel during a transient of the heat-up cycle; switching from the heat-up cycle, after the predetermined time period, to a cool-down cycle by forcing a cooled gas of a chosen temperature through the channel; measuring selected parameters from an infrared signature of the channel during a transient of the cool-down cycle; and detecting defects in the channel and identifying a nature of the defect by analyzing the measured parameters during both the heat-up transient and the cool-down transient.

In accordance with the invention, an apparatus for inspecting a channel includes a heater means for forcing a heated gas of a selected temperature through the channel for a predetermined time period to cause a heat-up cycle and a cooling means for forcing a chilled gas of a chosen temperature through the channel to cause a cool-down cycle. A valve means is provided for switching from the heat-up cycle, after the predetermined time period, to the cool-down cycle. An infrared radiometer is used to measure a transient of an infrared signature of the channel during both the heat-up cycle and the cool-down cycle. Defects in the channel can be determined by comparing the transient during both the heat-up and cool-down cycles to a known reference.

These and other objects of the present invention, together with the features and advantages thereof, will become apparent from the following specification when read with the accompanying drawings.

DETAILED DESCRIPTION OF THE PREFERRED EMBODIMENT

Figure 2:
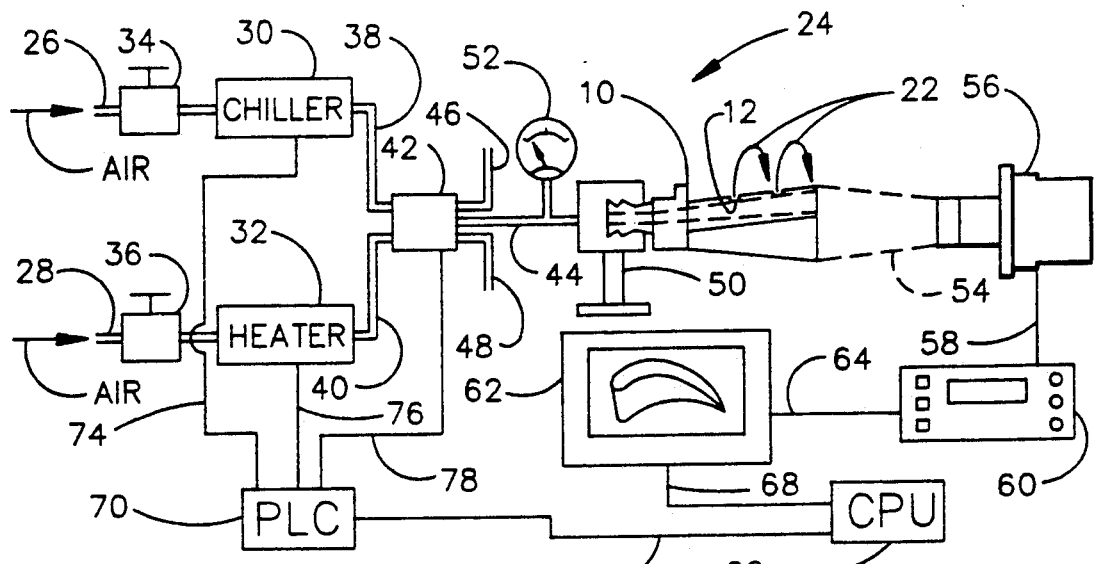
FIG. 2 is a schematic diagram of the nondestructive evaluation test setup in accordance with the present invention.

Referring initially to FIG. 2, a nondestructive evaluation (NDE) apparatus 24 for inspecting channels or cooling holes 12 formed in a workpiece or, in this example, a gas turbine engine blade 10 includes a first air line 26 and a second air line 28, both for receiving filtered, compressed air. The filter and air compressor arrangement are known, conventional constituents and are not shown in FIG. 2 for purposes of convenience. First air line 26 and second air line 28 are respectively connected to a chiller 30 and a heater 32 by respective pressure regulators 34 and 36. Chiller 30 and heater 32 are each respectively connected by output air lines 38 and 40 to a solenoid valve 42 which can be switched to alternatively provide heated air through feed line 44 during a heat-up cycle or chilled air through feed line 44 during a cool-down cycle. Chilled air is vented through a cool air vent 46 by solenoid valve 42 during a heat-up cycle and heated air may be vented through air vent 48 by solenoid valve 42 when valve 42 is switched to provide cool air through feed line 44. This is to permit air that is not passing through the workpiece to be maintained at a stable temperture, either heated or chilled, and a stable pressure.

Figure 1:
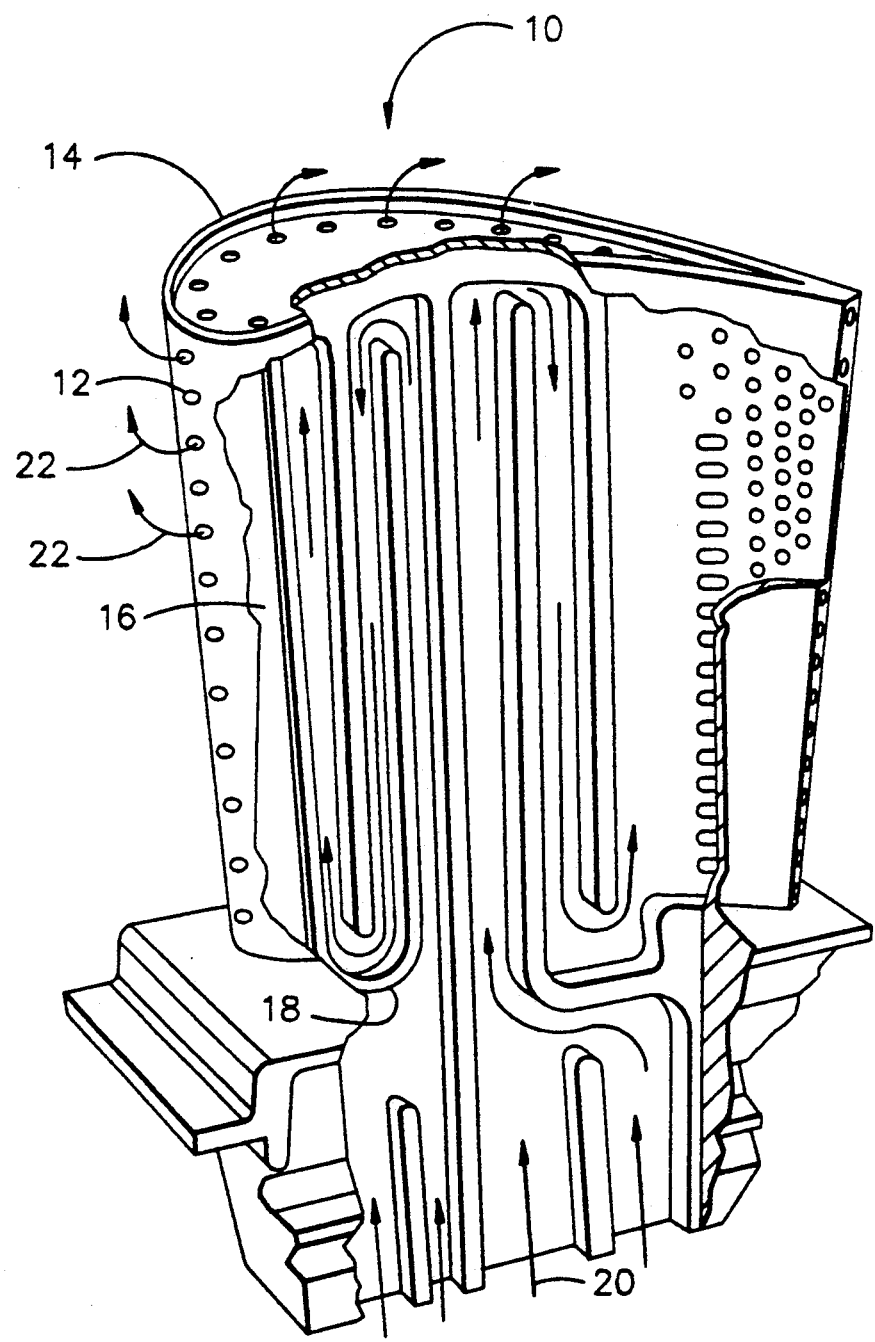
FIG. 1 is a perspective, partial cutaway view of a conventional gas turbine engine blade.

Feed line 44 is coupled to a fixture 50 to force either the heated air or the chilled air into the hollow interior 16 or plenum (FIG. 1) of blade 10. The pressurized chilled air 20 or warmed air 20 will then traverse through the interior baffles 18 of blade 10 and exit through cooling holes 12 as shown in FIG. 1. An in-line pressure gage 52 installed in feed line 44 may be provided to facilitate control of the pressure of the air entering the interior of blade 10.

Blade 10 is positioned by fixture 50 within an optical path 54 or within the field of view of a detector 56, such as an imaging infrared radiometer, infrared camera or the like. Detector 56 may be a Model 210 or a Model 525 imaging infrared radiometer as manufactured by Inframetrics, of Billerica, Mass.

Video signals from IR radiometer 56 are fed by a communications link 58 to a radiometer control 60 for adjusting the focus and contrast of IR radiometer 56. Radiometer control 60 is in turn interconnected to a video monitor 62 by a communications link 64. Video monitor 62 is interconnected to a Central Processing Unit (CPU) 66 by a communications link 68. CPU 66 may be a Digital Equipment Corporation (DEC) Model PDP-11/73 or the like with sufficient storage and computing capacity to store and analyze the infrared images received by IR radiometer 56.

CPU 66 is also interconnected to a Programmable Logic Controller (PLC) 70 by a communications link 72; PLC 70 may be a series 90 controller as manufactured by the General Electric Company or the like. PLC 70 is in turn respectively connected to chiller 30, heater 32, and solenoid valve 42 by communications links 74, 76 and 78 to control and coordinate the operation of these components.

In operation, the inspection of the cooling holes 12 of a gas turbine engine blade 10 will begin with a heat-up cycle by switching solenoid valve 42 to a position to switch heated air from vent 48 and to direct the heated air through feed line 44 to the interior of blade 10 while maintaining the venting of chilled air to the atmosphere through vent line 46. The air is heated by heater 32 to a temperature greater than ambient temperture to provide sufficient contrast in the infrared signature of the holes received by IR radiometer 56 when the heated air exits cooling hole 12. Heated air is preferably forced into the hollow interior of blade 10 for a predetermined time period to sufficiently heat the interior walls of blade 10 and the walls surrounding cooling holes 12. This time period will vary depending upon the size of the blade 10 but can be of a sufficient duration so that blade 10 is heated to a steady state condition or so that the blade material is heated to a sufficiently high temperature to cause a contrast in the infrared signature of the hcles detected by IR radiometer 56 when solenoid valve 42 is switched to provide chilled air to the interior of blade 10 for the cool-down cycle.

A series of infrared images of blade 10 are generated by IR radiometer 56 during the heat-up cycle. These images are displayed on video monitor 62 and are stored by CPU 66 for later analysis.

In accordance with the invention, after the heat-up cycle, solenoid valve 42 is switched to vent heated air to the atmosphere through vent line 48 and chilled air is immediately provided by chiller 30 to the interior of blade 10 by feed line 44 to start a cool-down cycle. The chilled air is preferrably below ambient to improve the contrast or sensitivity of the infrared signature received by IR radiometer 56. A second series of infrared images of blade 10 are generated by IR radiometer 56 during the cool-down cycle; these images are displayed on the video monitor 62 and stored by CPU 66 for later analysis.

The air streams 22 exiting cooling holes 12 during both the heat-up and cool-down cycles cause the cooling holes to act as black-body cavity radiators and as such, they approach behaving as idealized sources of radiation in accordance with Planck's well-known, empirically ascertained law.

Figure 3:
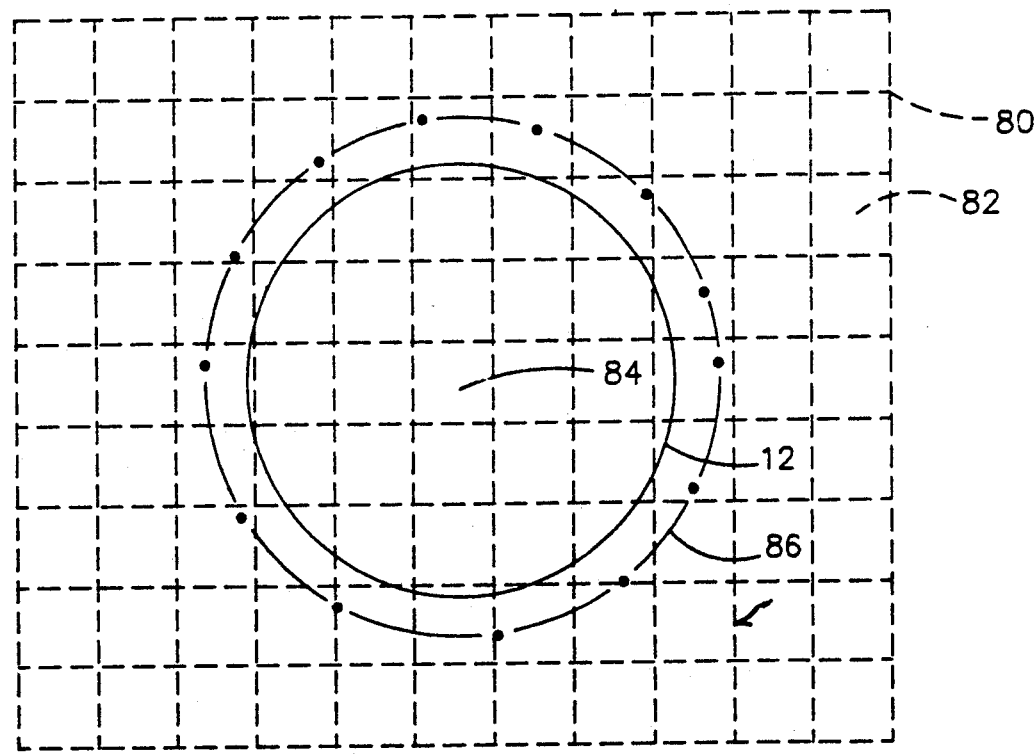
FIG. 3 is an illustration of an infrared image of a cooling hole, at the surface of a gas turbine engine blade, for inspection of the cooling hole in accordance with the present invention.

Referring now to FIG. 3, in accordance with the present invention, the series of infrared images generated and stored by CPU 66 during the heat-up cycle and cool-down cycle may each be divided into a grid 80, as illustrated by the crisscrossing broken lines in FIG. 3 which form a matrix of grid sections 82 arranged about a centroid 84. Only a single cooling hole 12 is shown in FIG. 3 for convenience and purposes of explanation. The relative intensities of radiation emitted by cooling hole 12 as either heated air or cooled air escapes through the cooling hole may be determined at selected times for each of the grid sections 82 from the series of images generated during the heat-up and cool-down cycles. Thus, a transient of the infrared signature of the cooling hole 12 may be measured during both the heat-up and cool-down cycles from the series of images generated by IR radiometer 56.

Selected parameters may be determined from the generated images and these different parameters may be analyzed in conjunction with one another and with a statistical base reference derived from the inspection of other turbine blades to determine whether a defect is present, and inferences may be drawn from analysis of the parameters as to the nature of the cooling hole defect.

Referring to FIG. 3, the selected parameters may include: (i) the radiation intensity proximate to the centroid 84 or the grid section located proximate to the geometric center of cooling hole 12; (ii) the average intensity across the entire cooling hole as determined by averaging the radiation intensity measured at each grid section 82 within the boundary of cooling hole 12; (iii)

the variation in the size of the radiative image of the boundary, as illustrated by chain line 86 in FIG. 3; the size of the area from which black-body radiation is emitted surrounding cooling hole 12 will expand and contract in response to the heated air exiting cooling hole 12 during the heat-up cycle and the cool air exiting cooling hole 12 during the cool-down cycle; and (iv) the time rate of change or transient response of the parameters described in (i), (ii) and (iii).

Figure 4:
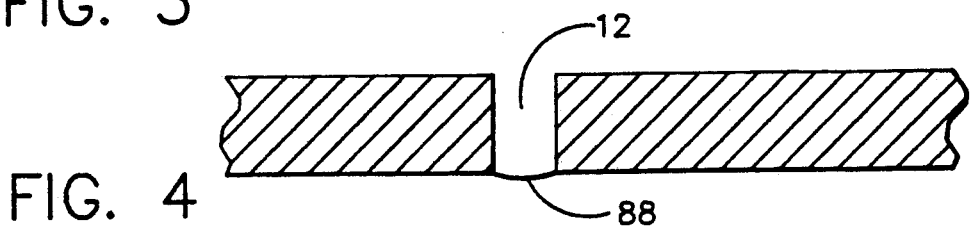
FIG. 4 is a cross-sectional view of a foil-blocked hole.

Hole defects, which may be inferred from the selected parameters, are: that the hole size is too small, the hole is completely blocked, the hole is partially blocked or the hole is completely or partially blocked by a thin layer or foil 86 of material as shown in FIG. 4. One disadvantage of prior art cooling hole inspection apparatuses and methods, that look at only a heat-up cycle, is that a cooling hole blocked by a thin layer of foil material 88 may be erroneously classified as a good, open hole because the foil-blocked hole may have an infrared signature similar to an open hole during the heat-up cycle. The foil-blocked hole defect becomes apparent, however, when both a heat-up cycle and a cool-down cycle are analyzed in tandem because the normalized radiation intensities of the foil-blocked hole will be higher compared to those of an open hole during the cool-down cycle.

Figure 5:
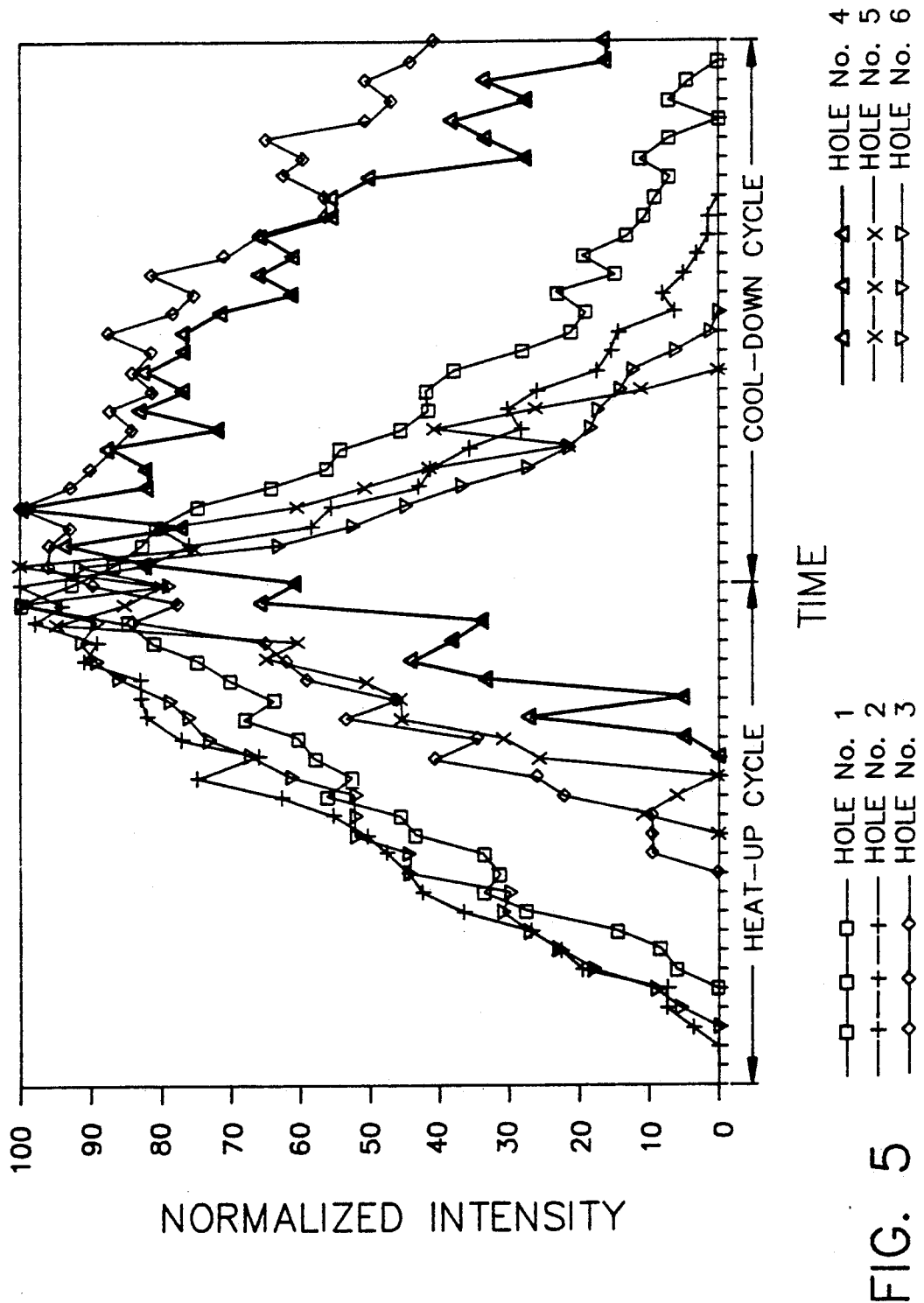
FIG. 5 is a series of graphs of the normalized radiation intensities of a selected number of cooling holes or channels of a gas turbine engine measured during a heat-up cycle and a cool-down cycle in accordance with the present invention.

FIG. 5 shows graphs of the normalized intensity of six cooling holes measured proximate to the centroid of each cooling hole during the heat-up cycle and the cool-down cycle. The intensity values are normalized in accordance with the following equation:

$$I_{norm} = \frac{100 \times I_t}{I_{max}}$$

where $I_{norm}$ is the normalized intensity, $I_t$ is the intensity at a selected time t, and $I_{max}$ is the maximum intensity value for the cooling hole over both heat-up and cool-down cycles. The normalization of the data enables a direct comparison between the data from holes on the same turbine blade and also permits direct comparison with the cooling holes on different turbine blades. The normalization also enhances the intensity differences between open and closed holes, particularly during the cool-down cycle. As can be seen from FIG. 5, the transient of holes 3, 4 and 5 lags behind the other cooling holes indicating that they are heating-up at a slower rate and may be blocked or defective. During the cool-down cycle, however, holes 3 and 4 are clearly distinguishable from the other holes and cool down at a much lower rate than the other holes which indicates that holes 3 and 4 are blocked. It should be noted that an erroneous conclusion may be drawn as to the condition of hole no. 5 if only the heat-up cycle is considered and those skilled in the art will recognize the advantages of analyzing both the heat-up cycle and the cool-down cycle in tandem. Applicant believes that hole no. 5 lags behind the other open holes and looks like a blocked hole during the heat-up cycle because it is down stream of blocked holes 3 and 4 and the air flow distribution of heated air is disrupted by the blocked holes.

Expansion of the air, whether it is heated or chilled, as the air exits channel or hole 12 will have a localized cooling effect in the area of channel or hole 12. This cooling effect may cause some decrease in sensitivity of the infrared images received by IR radiometer 56 during a heat-up cycle but will have an additive effect or improve sensitivity of the infrared signatures as received by IR radiometer 56 during the cool-down cycle. This is another advantage for looking at heat-up and cool-down cycles in tandem.

While the present invention has been described with regard to the inspection of cooling holes formed between the hollow interior 16 and the exterior surface 14 of a gas turbine engine blade 10 as shown in FIG. 1, those skilled in the art will recognize that the apparatus and method of the present invention may be used to detect defects in any type of hole or channel formed through a workpiece. Therefore, it will be readily understood by those skilled in the art that the present invention is not limited to the specific embodiments described and illustrated herein. Different embodiments and adaptations besides those shown herein and described, as well as many variations, modifications and equivalent arrangements will now be apparent or will be reasonably suggested by the foregoing specification and drawings, without departing from the substance or scope of the invention. While the present invention has been described herein in detail in addition to its preferred embodiment, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. A method of inspecting a channel, comprising the steps of:
    (a) forcing a heated gas of a selected temperature through the channel for a predetermined time period to cause a heat-up cycle;
    (b) measuring selected parameters from an infrared signature of the channel during a transient of the heat-up cycle;
    (c) switching from the heat-up cycle, after the predetermined time period, to a cool-down cycle by forcing a cooled gas of a chosen temperature through the channel;
    (d) measuring selected parameters from an infrared signature of the channel during a transient of the cool-down cycle; and
    (e) detecting defects in the channel and identifying a nature of the defect by analyzing the selected parameters from both the heat-up transient and the cool-down transient.

2. The method of claim 1, wherein step (e) comprises the step of comparing the selected parameters from both the heat-up transient and the cool-down transient with a reference.

3. The method of claim 1, wherein the selected temperature of the heated gas is greater than ambient temperature.

4. The method of claim 1, wherein the chosen temperature of the cooled gas is less than ambient temperature.

5. A method of inspecting cooling channels in a gas turbine engine blade, comprising the steps of:
    (a) forcing a heated gas of a selected temperature through the channels for a predetermined time period to cause a heat-up cycle;
    (b) viewing the channels with an imaging infrared radiometer and generating a first series of images which indicate the relative intensities of radiation emitted by the channels during the heat-up cycle;

(c) switching from the heat-up cycle, after the predetermined time period, to a cool-down cycle by forcing a cooled gas of a chosen temperature through the channels;

(d) viewing the channels with the imaging infrared radiometer and generating a second series of images which indicate the relative intensities of radiation emitted by the channels during the cool-down cycle; and (e) detecting defects in the channels and identifying a nature of the defect by analyzing the intensities of both the heat-up and cool-down cycles.

6. The method of claim 5, wherein step (e) comprises the step of comparing the intensities of both the heat-up and cool-down cycles with a reference.

7. The method of claim 6, wherein step (e) further comprises the step of normalizing the intensities to facilitate comparison.

8. The method of claim 5, wherein the selected temperature of the heated gas is greater than ambient temperature.

9. The method of claim 5, wherein the chosen temperature of the cooled gas is less than ambient.

10. A method of inspecting cooling holes in a gas turbine engine blade, comprising the steps of:

(a) forcing a heated gas of a selected temperature through the holes for a predetermined time period to cause a heat-up cycle;

(b) viewing the holes with an imaging infrared radiometer and generating a first series of images responsive to radiation emitted by the holes during the heat-up cycle;

(c) switching from the heat-up cycle, after the predetermined time period, to a cool-down cycle by forcing a cooled gas of a chosen temperature through the holes;

(d) viewing the holes with the imaging infrared radiometer and generating a second series of images responsive to radiation emitted by the holes during the cool-down cycle; and (e) detecting defects in any of the holes and identifying a nature of the defects by analyzing a group of selected parameters for each hole which are determined from the images generated during both the heat-up and cool-down cycles.

11. The method of claim 10, wherein the group of selected parameters includes:

(i) a radiation intensity determined at a centroid of each hole opening;

(ii) an average radiation intensity across the entire hole opening;

(iii) size of a radiative image from a boundary of each hole; and (iv) time rate of change of each of the parameters in (i), (ii) and (iii) during the heat-up and cool down cycles.

12. The method of claim 11, wherein step (e) comprises the step of comparing each of the parameters to a reference.

13. The method of claim 12, wherein step (e) further comprises the step of normalizing the parameters to facilitate comparison.

14. The method of claim 10, wherein the selected temperature of the heated gas is greater than ambient temperature.

15. The method of claim 10, wherein the chosen temperature of the cooled gas is less than ambient.

16. The method of claim 10, wherein the predetermined time period is before the holes are heated to a steady-state temperature.

17. The method of claim 10, wherein the predetermined time period is after the holes are heated to a steady-state temperature.

18. An apparatus for inspecting a channel, comprising:

means for forcing a heated gas of a selected temperature through the channel for a predetermined time period to cause a heat-up cycle;

valve means for switching from said heat-up cycle, after said predetermined time period, to a cool-down cycle by forcing a chilled gas of a chosen temperature through the channel;

means for measuring a transient of an infrared signature of the channel during both said heat-up cycle and said cool-down cycle; and means for detecting a defect in the channel by comparing said transient during both said heat-up and cool-down cycles to a known reference.

19. An apparatus for inspecting a channel formed through a workpiece, comprising:

a heater means for supplying a heated gas at a selected temperature to cause a heat-up cycle;

a chiller means for supplying a chilled gas at a chosen temperature to cause a cool-down cycle;

a valve means for switching between the heat-up cycle and the cool-down cycle, said valve means being connected respectively to an output of said heater means and said chiller means;

an imaging infrared radiometer for receiving infrared radiation from the channel during the heat-up and cool-down cycles;

fixture means for holding the workpiece in an optical path of the radiometer and for directing the heated and cooled gas through the channel during the heat-up and cool-down cycles; and means for generating a series of images corresponding to the radiation received by the radiometer and detecting defects by analyzing a group of selected parameters which are determined from the images generated during both the heat-up and cool-down cycles.

* * * * *